(12) United States Patent
Zhang et al.

(10) Patent No.: US 12,005,431 B2
(45) Date of Patent: Jun. 11, 2024

(54) SYSTEM, METHOD, AND REACTION APPARATUS USED FOR CONTINUOUS REACTION PROCESS FOR PREPARATION OF TRIFLUOROETHANE

(71) Applicants: ZHEJIANG QUHUA FLUOR-CHEMISTRY CO., Ltd., Hangzhou (CN); Beijing University of Chemical Technology, Beijing (CN); Juhua Group Co., Ltd, Hangzhou (CN)

(72) Inventors: Liangliang Zhang, Beijing (CN); Liyang Zhou, Hangzhou (CN); Guangwen Chu, Beijing (CN); Jihong Tong, Hangzhou (CN); Jianfeng Chen, Beijing (CN); Jiangyong Hong, Hangzhou (CN); Bo Yang, Hangzhou (CN)

(73) Assignees: ZHEJIANG QUHUA FLUOR-CHEMISTRY Co., Ltd., Hangzhou (CN); Beijing University of Chemical Technology, Beijing (CN); Juhua Group Co., Ltd, Hangzhou (CN)

(*) Notice: Subject to any disclaimer, the term of this patent is extended or adjusted under 35 U.S.C. 154(b) by 0 days.

(21) Appl. No.: 18/038,531

(22) PCT Filed: Nov. 29, 2021

(86) PCT No.: PCT/CN2021/133977
§ 371 (c)(1),
(2) Date: May 24, 2023

(87) PCT Pub. No.: WO2022/111685
PCT Pub. Date: Jun. 2, 2022

(65) Prior Publication Data
US 2024/0017231 A1 Jan. 18, 2024

(30) Foreign Application Priority Data
Nov. 27, 2020 (CN) .......................... 202011359017.8

(51) Int. Cl.
*B01J 8/10* (2006.01)
*C07C 17/25* (2006.01)

(52) U.S. Cl.
CPC .................. *B01J 8/10* (2013.01); *C07C 17/25* (2013.01)

(58) Field of Classification Search
CPC ...... B01J 8/10; B01J 19/0066; B01J 19/0063; B01J 19/1887; B01J 3/008; B01J 3/004;
(Continued)

(56) References Cited

U.S. PATENT DOCUMENTS
2006/0182673 A1  8/2006  Hensman

FOREIGN PATENT DOCUMENTS
CN  104140353      11/2014
CN  104140353  A  11/2014
(Continued)

OTHER PUBLICATIONS
Zhang et al., CN 112705125 A, English translation, published Apr. 27, 2021.*
(Continued)

*Primary Examiner* — Jafar F Parsa
(74) *Attorney, Agent, or Firm* — Rankin, Hill & Clark LLP

(57) ABSTRACT

A reaction apparatus used for a continuous reaction process for the preparation of trifluoroethane includes a housing, a rotary cutting component, a submersible pump and a flow deflector. The flow deflector includes two sets of flow-deflecting plates, each set of said flow-deflecting plates including a plurality of flow-deflecting plates. Two sets of flow-deflecting plates are fixed to each of the two opposing side walls, and the two adjacent flow-deflecting plates are in offset alignment. The submersible pump is arranged inside the reaction chamber body. A liquid inlet line can connect a
(Continued)

directly to the submersible pump without requiring the arrangement of an additional pipeline.

6 Claims, 4 Drawing Sheets

(58) Field of Classification Search
CPC .......... B01J 3/002; C07C 17/25; C07C 17/21; C07C 17/087; C07C 17/38; C07C 19/08
See application file for complete search history.

(56) References Cited

FOREIGN PATENT DOCUMENTS

| | | |
|---|---|---|
| CN | 105688752 | 6/2016 |
| CN | 206008715 | 3/2017 |
| CN | 206008715 U | 3/2017 |
| CN | 106732210 | 5/2017 |
| CN | 106943978 | 7/2017 |
| CN | 109647315 | 4/2019 |
| CN | 112705125 | 4/2021 |

OTHER PUBLICATIONS

Guo et al., States-of-the arts progress on fundamental research and industrial applications of rotating packed bed, Chemical Industry and Engineering Progress, Dec. 31, 2018, 12 pages.
China National Intellectual Property Office, First Office action issued in CN 202011359017.8 mailed Jan. 26, 2022, 10 pages.
International Search Report filed in PCT/CN2021/133977 dated Feb. 22, 2022.

* cited by examiner

SYSTEM, METHOD, AND REACTION APPARATUS USED FOR CONTINUOUS REACTION PROCESS FOR PREPARATION OF TRIFLUOROETHANE

TECHNICAL FIELD

The present application relates to the technical field of chemical engineering, in particular to a system, method and reaction apparatus used for continuous reaction process for preparation of trifluoroethane.

BACKGROUND 1,1,1-trifluoroethane (HFC-143a) is a third-generation of new environmentally friendly refrigerant and an important component of new type of mixed refrigerants R404A and R507 that replace R502. At present, the main approaches for producing HFC-143a include an HCFC-141b approach, an HCFC-142b approach, and a vinylidene chloride approach. Their production processes are divided into a gas phase method and a liquid phase method. The addition and fluorination method of vinylidene chloride has become the mainstream process for industrial production of HFC-143a due to its cheap and easily available raw materials and low production costs.

The reaction formulas are as follows:

  Addition 1

  Substitution 2

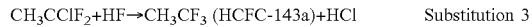  Substitution 3

According to existing kinetic data, reaction 1 is a fast reaction that can be completed within seconds, while reaction 2 and reaction 3 are relatively slow and require several hours for completion. During reaction, vinylidene chloride is prone to self-polymerization side reactions, affecting the utilization rate of raw materials. Meanwhile, the resulting polymer is prone to encapsulate catalyst molecules, affecting the progress of the main reaction.

The current mainstream production process is carried out in a regular stirred reaction kettle, with the entire system maintained at high pressure and the reaction kettle temperature maintained at around 90° C. Raw hydrogen fluoride liquid and vinylidene chloride liquid are fed into the reaction kettle, addition and substitution reactions continuously occur under the action of the catalyst in the reaction kettle. Because the boiling points of the intermediate product HCFC-142b, the product HCFC-143a and the by-product hydrogen chloride are low, they are evaporated from the reaction kettle after generation, and then separated by condensation. The intermediate product HCFC-142b with a higher boiling point is condensed into liquid and returned to the reaction kettle for further reaction. The product HCFC-143a and by-product hydrogen chloride are extracted in a gaseous state and then subjected to subsequent distillation and separation.

SUMMARY

In order to solve at least one of the defects mentioned above, an embodiment of the present application provides a reaction apparatus, comprising:
a housing comprising a reaction chamber body and a gas exit passageway in communication with the reaction chamber body;
a rotary cutting component arranged inside the reaction chamber body, used for cutting a fluid into micro/nanoscale fluid micro elements;
a submersible pump arranged at a bottom of the reaction chamber body; and
a flow deflector comprising two sets of flow-deflecting plates, each set of said flow-deflecting plates comprising a plurality of flow-deflecting plates, the two sets of flow-deflecting plates being respectively fixed on two opposing sidewalls, and adjacent two flow-deflecting plates being in offset alignment, wherein
the submersible pump is coupled with a discharge pipeline, and the rotary cutting component is coupled with a feed pipeline.

In a preferred embodiment, each flow-deflecting plate is tilted upwards along a direction towards the sidewall on which the flow-deflecting plate is fixed.

In a preferred embodiment, a plurality of protrusions are formed on a lower surface of each flow-deflecting plate.

In a preferred embodiment, the diameter of the protrusion gradually increases along a direction towards the corresponding sidewall.

In a preferred embodiment, the reaction apparatus further comprises:
a condensation disturbance component comprising a rotating shaft and a condenser surrounding the rotating shaft, the rotating shaft being used for throwing condensed liquid drops on the condenser into the rotary cutting component.

In a preferred embodiment, the rotary cutting component comprises an annular filler and a liquid distributor located in a center of the annular filler, and threads are formed on a surface of the annular filler.

In a preferred embodiment, each set of said flow-deflecting plates comprises 3-25 flow-deflecting plates.

The present application further provides a system for preparing trifluoroethane through continuous reaction, comprising:
a vinylidene chloride liquid feed pipeline and a hydrogen fluoride feed pipeline, the vinylidene chloride liquid feed pipeline and the hydrogen fluoride feed pipeline being in communication with the rotary cutting component and the submersible pump of the reaction apparatus.

In a preferred embodiment, the system further comprises:
a condensing component in communication with the gas exit passageway gas exit passageway of the reaction apparatus.

The present application further provides a method for preparing trifluoroethane through continuous reaction, comprising:
pumping vinylidene chloride and hydrogen fluoride into the submersible pump and the rotary cutting component of the reaction apparatus according to a set ratio through a first liquid feed pipeline;
pumping a fluid entraining catalyst particles into the rotary cutting component through a circulating pipeline, so that the rotary cutting component cuts the fluid entraining the catalyst particles into micro/nanoscale fluid micro elements and thereby the catalyst particles catalyze the vinylidene chloride and hydrogen fluoride to generate trifluoroethane; and
heating the reaction apparatus to a set temperature through a jacket arranged on an outer sidewall of the reaction apparatus such that trifluoroethane is discharged through the gas exit passageway.

Beneficial Effects of the Present Application

The present application provides a system, method and reaction apparatus for preparing trifluoroethane through continuous reaction. The reaction apparatus comprises combination use of a submersible pump and a flow deflector. The flow deflector comprises two sets of flow-deflecting plates. Each set of said flow-deflecting plates comprises a plurality of flow-deflecting plates. The two sets of flow-deflecting plates are respectively fixed on opposing two sidewalls, and adjacent two flow-deflecting plates are in offset alignment. On the one hand, the submersible pump is arranged inside a reaction chamber body and a liquid inlet pipeline can be directly connected to the submersible pump without providing an additional pipeline, thus avoiding the problem that a pump arranged outside cannot maintain sufficient pressure during high-pressure reaction, and enhancing the reaction safety factor. Meanwhile, the flow-deflecting plates are arranged at a gas exit passageway of a reactor, thus integrating gas-liquid separation. Integration of equipment is suitable for high-pressure reaction. The reaction apparatus arranged of the present application is particularly suitable for the preparation of, for example, 1,1,1-trifluoroethane (HFC-143a).

DESCRIPTION OF THE DRAWINGS

The embodiments of the present application will be further described below in detail with reference to the drawings.

DESCRIPTION OF REFERENCE SIGNS

Figure 1:
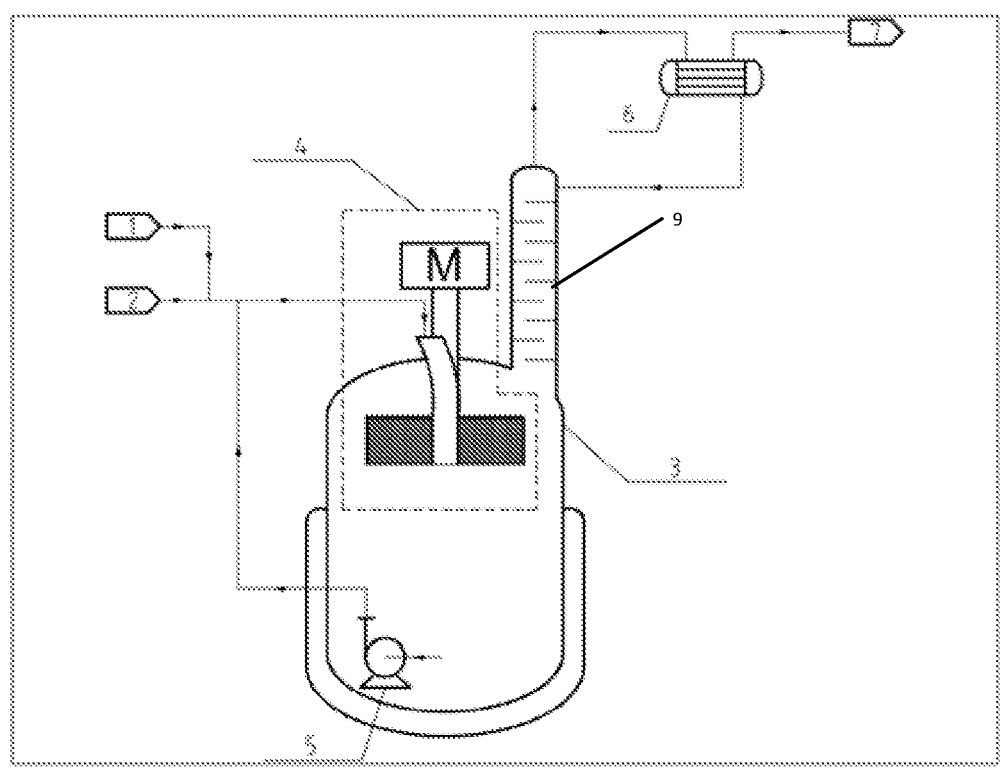
FIG. 1 illustrates a schematic structural diagram of a system for preparing trifluoroethane through continuous reaction in an embodiment of the present application.

1—vinylidene chloride inlet; 2—hydrogen fluoride inlet; 3—jacket reaction kettle with flow—deflecting plates at top of the reaction kettle; 4—built-in high-gravity reactor; 5—submersible pump; 6—condenser; 7—product HFC-143a and by-product hydrogen chloride outlet; 8—condensation disturbance component; 10—flow—deflecting plate; 11—protrusion

DETAILED DESCRIPTION

In order to describe the present application more clearly, the present application will be further described below in combination with preferred embodiments with reference to the drawings. Like components in the drawings are represented by like reference signs. Those skilled in the art should understand that the specific description below is descriptive rather than restrictive and should not limit the scope of protection of the present application.

Various cross-sectional views according to the disclosed embodiments of the present application are illustrated in the drawings. These drawings are not drawn to scale, and for the purpose of expression clarity, certain details have been enlarged and may have been omitted. The shapes of various regions and layers illustrated in the drawings, as well as their relative sizes and positional relationships, are only exemplary. In practice, there may be deviations due to manufacturing tolerances or technical limitations. Those skilled in the art can additionally design regions/layers with different shapes, sizes, and relative positions according to actual needs.

At present, the publicly reported process for preparing HCFC-143a through addition and fluorination method of vinylidene chloride has the following problems:

(1) The utilization rate of raw materials is low and the amount of polymers is large. Due to the unsatisfactory mixing effect of the existing process, the raw material vinylidene chloride is locally excessive, the addition reaction cannot be completed, the materials stay in the reaction kettle for a long time, it is prone to self-polymerization of vinylidene chloride to generate a large amount of polymers and tar-like substances, and the utilization rate of raw materials is low. According to research, the utilization rate of raw material vinylidene chloride in the existing process is only around 90%.

(2) The production efficiency is low and frequent shut-down for maintenance is required. The large amount of polymers and tar-like substances generated by the self-polymerization of vinylidene chloride described above will coat on the surface of the equipment and catalyst, making the catalyst coagulate and difficult to effectively disperse in the reaction system, reducing the efficiency of the reaction, and requiring frequent shut-down to remove the tar-like substances and replace the catalyst.

(3) The separation effect is poor and the product purity is low. Due to poor mixing effect in the reaction kettle, the existing process results in low product content in the rising steam, making subsequent separation difficult and resulting in low product purity. According to research, the mass fraction of HCFC-143a in the outlet gas (containing no hydrogen chloride gas) in the existing process is less than 95%.

(4) The energy consumption for reaction and separation is high. The existing process has poor mixing effect in the reaction kettle, resulting in uneven heating and poor heat transfer effect. In the subsequent separation process, the intermediate product HCFC-142b in the condensation reflux of the steam does not have sufficient contact with the rising steam, resulting in untimely heat exchange and insufficient utilization of the system's heat and cooling capacity.

For the reasons above, the present application firstly provides a apparatus particularly for preparing trifluoroethane through continuous reaction. Referring to FIG. 1, the apparatus comprises a housing 2 comprising a reaction chamber body and a gas exit passageway in communication with the reaction chamber body;

A rotary cutting component 4 arranged inside the reaction chamber body and used for cutting a fluid into micro/nanoscale fluid micro elements;

A submersible pump 5 arranged at a bottom of the reaction chamber body; and

A flow deflector 9 comprising two sets of flow-deflecting plates, each set of said flow-deflecting plates comprising a plurality of flow-deflecting plates, the two sets of flow-deflecting plates being respectively fixed on opposing sidewalls, and adjacent two flow-deflecting plates being in offset alignment, wherein The submersible pump 5 is coupled with a discharge pipeline, and the rotary cutting component is coupled with a feed pipeline.

The present application provides a reaction apparatus for preparing trifluoroethane through continuous reaction. The reaction apparatus comprises a submersible pump and a flow deflector which are combined for use. The flow deflector comprises two sets of flow-deflecting plates. Each set of said flow-deflecting plates comprises a plurality of flow-deflecting plates. The two sets of flow-deflecting plates are respectively fixed on opposing sidewalls, and adjacent flow-deflecting plates are in offset alignment. On the one hand, the submersible pump is arranged inside a reaction chamber body and a liquid inlet pipeline can be directly connected to the submersible pump without requiring the arrangement of an additional pipeline, thus avoiding the problem that a pump arranged outside cannot maintain sufficient pressure during high-pressure reaction, and enhancing the reaction safety factor. Meanwhile, the flow-deflecting plates are arranged at a gas exit passageway of a reactor, thus integrating gas-liquid separation, this integrated equipment is suitable for high-pressure reaction. The reaction apparatus arranged by the present application is particularly suitable for the preparation of, for example, 1,1,1-trifluoroethane (HFC-143a).

It is to be understood that the reaction apparatus arranged by the present application is developed for preparing trifluoroethane through continuous reaction, but the reaction apparatus arranged herein can also be applied to other reaction systems similar to systems for preparing trifluoroethane through continuous reaction. In summary, the reaction apparatus arranged herein can be applied to high-pressure gas-liquid reaction systems.

In a preferred embodiment, each flow-deflecting plate is tilted upwards along a direction towards the sidewall on which the flow-deflecting plate is fixed. In the present application, the flow-deflecting plate is tilted and the condensed liquid drops can drip down along the flow, thus helping to gather the liquid drops.

Figure 3:
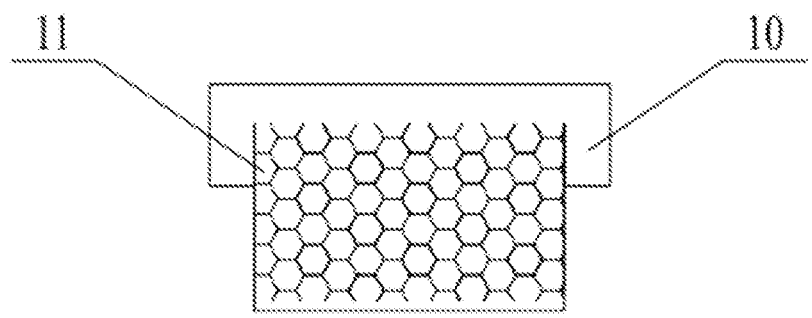
FIG. 3 is a schematic structural diagram of flow-deflecting plates in an embodiment of the present application.
Figure 4:
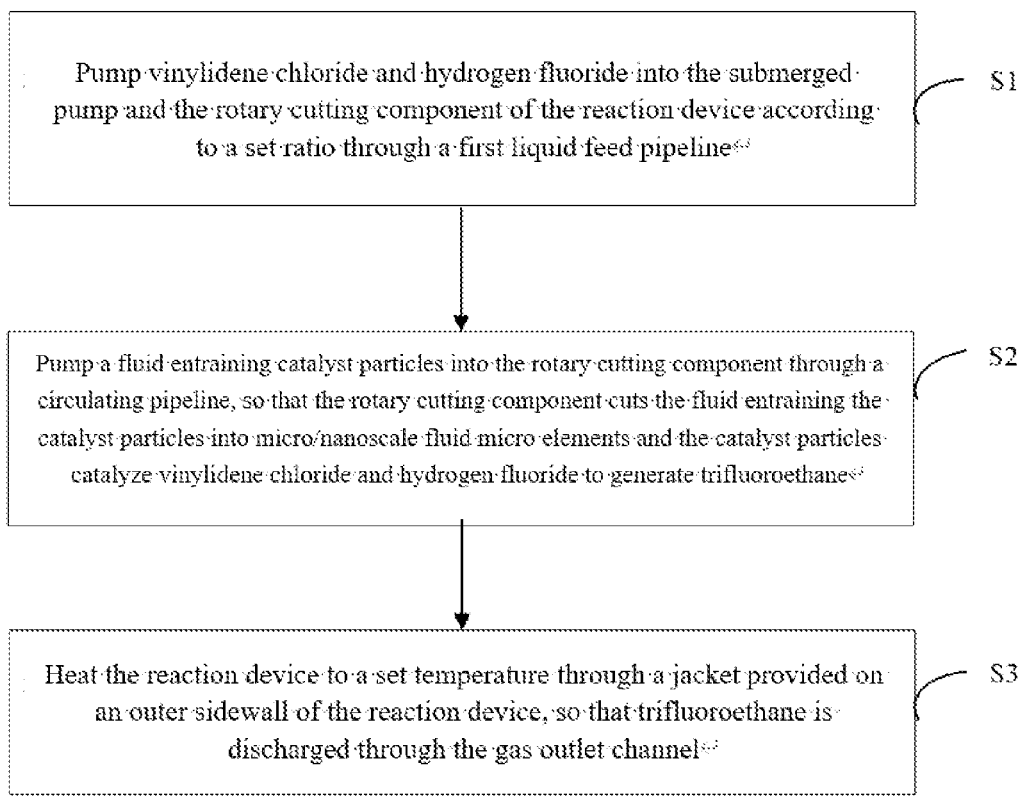
FIG. 4 is a flowchart of method for preparing trifluoroethane through continuous reaction in an embodiment of the present application.

In order to further achieve the purpose of gathering the liquid drops, as illustrated in FIG. 3, a plurality of protrusions 11 are formed on a lower surface of each flow-deflecting plate 10. In this way, the liquid drops can temporarily "stay" in gaps between the protrusions, thus lowering the temperature of the entire flow-deflecting plate and helping to accelerate the gathering speed of the liquid drops.

In some preferred embodiments, in order to avoid the overflow of the liquid drops at the end of the flow-deflecting plates, the diameter of the protrusion gradually increases along a direction towards the corresponding sidewall. On the one hand, the gaps between the protrusions are larger, thus accommodating more liquid drops, further lowering the temperature of the flow-deflecting plates at the end, and helping to prevent the liquid drops from overflowing from the reaction outlet channel.

Figure 2:
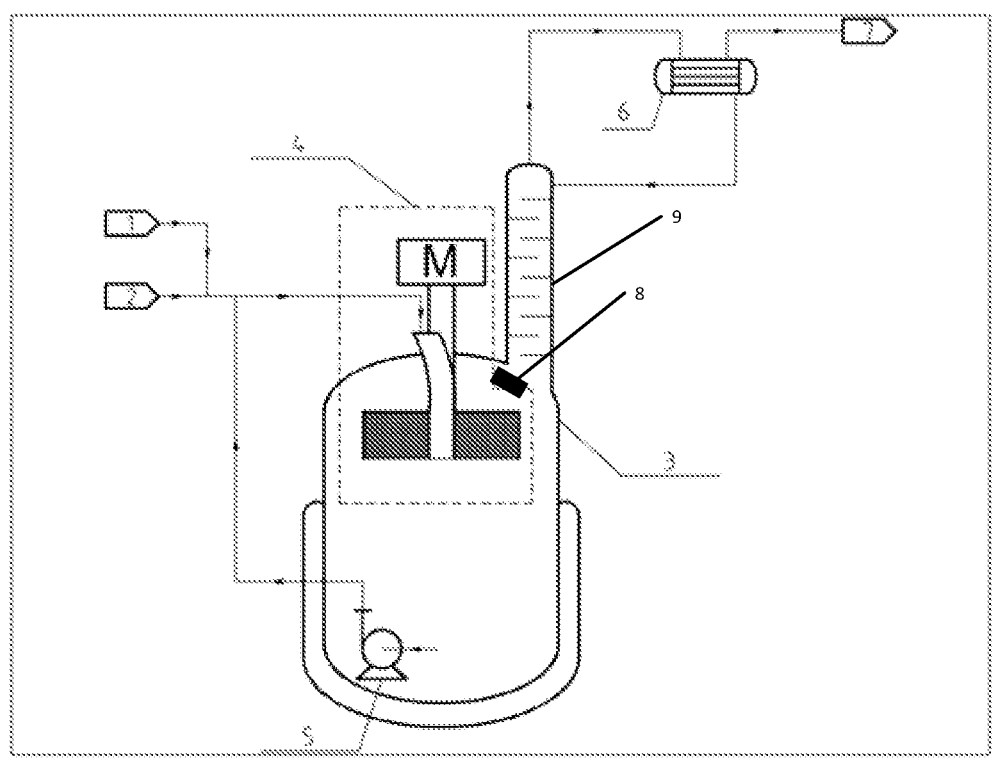
FIG. 2 illustrates a schematic structural diagram of a system for preparing trifluoroethane through continuous reaction in an embodiment of the present application.

In addition, in a further preferred embodiment of the present application, referring to FIG. 2, the reaction apparatus further comprises a condensation disturbance component comprising a rotating shaft and a condenser surrounding the rotating shaft. The rotating shaft is used for throwing condensed liquid drops on the condenser into the rotary cutting component.

On the one hand, the condensation disturbance component can cooperate with the flow-deflecting plates to form secondary condensation. On the other hand, the disturbance component can directly throw the liquid drops into the rotary cutting component. The condensed liquid drops are cut and atomized again, thus strengthening the mixing effect again. Moreover, due to the lower temperature of the liquid drops after condensation, they can be kept inside the reaction chamber body for a longer time after atomization, thus increasing the residence time of gas in the atomized liquid drops and enhancing the reaction efficiency.

In addition, in a preferred embodiment, the rotary cutting component comprises an annular filler and a liquid distributor located in a center of the annular filler, and threads are formed on a surface of the annular filler. In this embodiment, the threads are formed on the surface of the filler, which on the one hand have the function of "locking" the nano catalyst and help to lock the nano catalyst particles or crushed catalyst particles onto the surface of the filler in the reaction process, thus forming a "fixed catalyst filler" in the continuous reaction process, and making it especially suitable for systems with longer catalyst life.

Further, in some embodiments, each set of said flow-deflecting plates comprises 3-25 flow-deflecting plates. Of course, the flow-deflecting plates in the present application may be freely arranged as needed, and the present application is not limited thereto.

It is to be understood that the rotary cutting component in the present application achieves shearing and crushing the reaction solution to form micro/nanoscale fluid micro elements through the shear effect of the rotary filler. The shear effect of the rotary filler can effectively enhance the gas-liquid mixing effect. In the present application, the defined range of micro/nanoscale is less than 100 microns, i.e., between 1 nm-100 um.

The present application will be continuously described below in detail with reference to FIG. 1. It is to be understood that FIG. 1 is only one specific example of the present application, and certain specific apparatuses or structures thereof may not necessarily be necessary apparatuses or structures for the continuous sugar production process of the present application. Other well-known apparatuses or structures obtained based on the core concept of the present application by replacing one or more of the present application should also fall within the scope of protection of the present application.

For example, in the embodiment illustrated in FIG. 1, the apparatus mainly comprises a built-in high-gravity reactor (i.e., the rotary cutting component 4 described above), a jacket reaction kettle with flow-deflecting plates at a top of the reaction kettle (i.e., the housing 3 described above), and a submersible pump 5. The assembling method is as follows: the built-in high-gravity reactor is placed in an upper space of the inner chamber of the jacket reaction kettle with flow-deflecting plates at the top of the reaction kettle, and the submersible pump 5 is placed in a lower space of the inner chamber of the jacket reaction kettle with flow-deflecting plates at the top of the reaction kettle. Specifically, the piece number of flow-deflecting plates at the top of the reaction kettle is 3-25, preferably 5-10.

When in specific use, the raw materials vinylidene chloride 1 and hydrogen fluoride 2 are continuously fed into a feed port of the built-in high-gravity reactor according to a certain ratio, which, together with the catalyst liquid entrained in the circulating feed liquid, are sheared and crushed into liquid drops, liquid filaments and liquid films in the rotary filler, fully mixed and quickly reacted. After passing through the high-gravity reactor, the reaction liquid and the catalyst enter the lower space of the inner chamber of the jacket reaction kettle with flow-deflecting plates at the top of the reaction kettle. The reaction kettle is heated by jacket steam to maintain a certain temperature. The product 1,1,1-trifluoroethane (HFC-143a), the intermediate product 1,1-difluoroethane (HCFC-142b), and mixed gas obtained through gasification of the by-product hydrogen chloride are evaporated from the top of the reaction kettle through the flow-deflecting plates. The liquid at the bottom of the reaction kettle is circulated back to the high-gravity reactor through the submersible pump 5 for continuous reaction. In the flow-deflecting plates at the top of the reaction kettle, the mixed gas and the reflux condensate are in countercurrent contact. The heavy component 1,1-difluoroethane (HCFC-142b) in the gas is mostly condensed and washed into the liquid phase, and the mixed gas is further refined. The refined mixed gas flows out of the flow-deflecting plates at the top of the reaction kettle and is fed into the condenser 6. In the condenser, impurities such as intermediate product 1,1-difluoroethane (HCFC-142b) with high boiling points are condensed, which, as the aforementioned reflux liquid, are returned to the reaction kettle through the flow-deflecting plates at the top of the reaction kettle. The product 1,1,1-trifluoroethane (HFC-143a) and by-product hydrogen chloride gas are discharged from a gas phase outlet of the condenser and directed to a subsequent refining separation unit, thus obtaining high-purity product 1,1,1-trifluoroethane (HFC-143a) and by-product hydrogen chloride.

Specifically, the level of the high gravity field in the high-gravity reactor is 30-1500 g, more preferably 100-600 g. The temperature of the reaction kettle is maintained at 60-110° C., preferably 80-90° C. The pressure of the reaction kettle is maintained at 1.2 MPa. The molar flow ratio of raw materials hydrogen fluoride to vinylidene chloride fed into the high-gravity reactor is 2-5:1, more preferably 3-4:1. The ratio of the mass flow of the circulating liquid passing through the submersible pump to the sum of the mass flow of the newly fed raw materials vinylidene chloride and hydrogen fluoride is 5-15:1, more preferably 8-10:1. The liquid-phase catalyst comprises but is not limited to $SnCl_4$, halosulfonic acid, and a mixture thereof. The mass ratio of the catalyst molecules in the liquid-phase catalyst in the circulating liquid to the newly fed vinylidene chloride is 0.1-0.3:1.

It is to be understood that the embodiment of the present application has the following effects:
1. The reaction efficiency is improved and the utilization rate of raw materials is enhanced. Since the reaction feed liquid is quickly mixed after entering the high-gravity reactor, part of the coagulated and coated catalyst micelles are crushed, the active site of the catalyst is fully exposed, and the reaction is fast. Moreover, since there is a large amount of unreacted hydrogen fluoride contained in the circulating liquid, the hydrogen fluoride is therefore too excessive in the reaction process. The above two reasons result in vinylidene chloride being rapidly reacted, thus inhibiting the self-polymerization and significantly improving the utilization rate of raw materials. After adopting the present application, the utilization rate of raw material vinylidene chloride can reach more than 98%.
2. The production efficiency and safety are improved. As described above, the present application can effectively inhibit the occurrence of the self-polymerization side reaction of vinylidene chloride, prevent the polymers and tar-like substances generated by self-polymerization from coating the equipment and catalyst, and ensure long-term continuous production without frequent shut-down for maintenance. Hydrogen fluoride leakage is a very serious safety accident. The present application uses the built-in submersible pump to reduce the risk of leakage of a large amount of hydrogen fluoride in the circulating liquid. In addition, the present application couples the separation apparatus (flow-deflecting plates at the top of the reaction kettle) with the reaction kettle to reduce the risk of leakage during pipeline transportation. Therefore, the safety of the present application is relatively high.
3. The separation effect is good and the product purity is high. The unique design of the flow-deflecting plates at the top of the reaction kettle in the present application allows for full contact and heat exchange between the reflux condensate and the rising gas. The heavy component impurities entrained in the steam are washed into the reflux liquid, and a small amount of condensed products in the reflux liquid are evaporated into the gas, thus improving the purity of the product. After adopting the present application, the mass fraction of HFC-143a in the product can reach 98% (containing no by-product hydrogen chloride).
4. The energy utilization rate is enhanced and the equipment size is reduced. The present application integrates the high-gravity reactor, the high-pressure kettle and the rectifying tower as one equipment, thus reducing the heat and momentum loss during the transfer of materials between equipment, improving the energy utilization rate, and reducing the total foot print of the apparatus by more than half.

In a preferred embodiment, the rotary cutting component may be arranged based on the rotary packed bed or the stator-rotor reactor. In this preferred embodiment, it is arranged based on the rotary packed bed. In some specific embodiments, it is used in a system for preparing trifluoroethane through continuous reaction. The rotary cutting component comprises a rotating chamber, a filler, and a housing of the rotating chamber surrounding the filler. The housing of the rotating chamber is fixedly connected to a rotating shaft, which can rotate under the drive of the rotating shaft. A central part of the pacing is a hollow structure, into which a liquid distributor is inserted. Liquid or solid-liquid mixed fluid can be sprayed onto the filler through the liquid distributor, and the rotary filler can cut the liquid or solid-liquid mixed fluid, thus forming micro/nanoscale fluid micro elements in the chamber and therefore achieving the sufficient pre-mixing effect.

Further, in order to ensure the sealing performance, a sealing apparatus may be arranged, which will not be described here.

The rotary cutting component of the system for preparing trifluoroethane through continuous reaction is driven by a motor connected to the rotating shaft. The model or type of the motor is not limited in the present application.

The micro/nanoscale in the embodiment of the present application should be understood as microscale or nanoscale, that is, a range from 1 nm to 100 um belongs to the micro/nanoscale.

In some embodiments, the material of the filler is nickel, copper, stainless steel, etc. For example, the filler is stainless steel wire mesh, copper mesh, foam copper or foam ceramic. The material of the filler may also be cordierite, sepiolite, foam ceramic, foam nickel or $Al_2O_3$, which is not limited in the present application.

In some embodiments, the rotating speed of the rotary cutting component in the system used for preparing trifluoroethane through continuous reaction is 600 rpm, 800 rpm, 1200 rpm or 1600 rpm, which is not limited in the present application.

The present application further provides a system for preparing trifluoroethane through continuous reaction, comprising: a vinylidene chloride liquid feed pipeline and a hydrogen fluoride feed pipeline. The vinylidene chloride liquid feed pipeline and the hydrogen fluoride feed pipeline are in communication with the rotary cutting component and the submersible pump of the reaction apparatus described above.

It is to be understood that the system for preparing trifluoroethane through continuous reaction arranged by the present application has the following advantages:

1. The reaction efficiency is improved and the utilization rate of raw materials is enhanced. Since the reaction feed liquid is quickly mixed after entering the high-gravity reactor, part of the coagulated and coated catalyst micelles are crushed, the active site of the catalyst is fully exposed, and the reaction is fast. Moreover, since there is a large amount of unreacted hydrogen fluoride contained in the circulating liquid, the hydrogen fluoride is therefore too excessive in the reaction process. The above two reasons result in vinylidene chloride being rapidly reacted, thus inhibiting the self-polymerization and significantly improving the utilization rate of raw materials. After adopting the present application, the utilization rate of raw material vinylidene chloride can reach more than 98%.
2. The production efficiency and safety are improved. As described above, the present application can effectively inhibit the occurrence of the self-polymerization side reaction of vinylidene chloride, prevent the polymers and tar-like substances generated by self-polymerization from coating the equipment and catalyst, and ensure long-term continuous production without frequent shut-down for maintenance. Hydrogen fluoride leakage is a very serious safety accident. The present application uses the built-in submersible pump to reduce the risk of leakage of a large amount of hydrogen fluoride in the circulating liquid. In addition, the present application couples the separation apparatus (flow-deflecting plates at the top of the reaction kettle) with the reaction kettle to reduce the risk of leakage during pipeline transportation. Therefore, the safety of the present application is relatively high.
3. The separation effect is good and the product purity is high. The unique design of the flow-deflecting plates at the top of the reaction kettle in the present application allows for full contact and heat exchange between the reflux condensate and the rising gas. The heavy component impurities entrained in the steam are washed into the reflux liquid, and a small amount of condensed products in the reflux liquid are evaporated into the gas, thus improving the purity of the product. After adopting the present application, the mass fraction of HFC-143a in the product can reach 98% (containing no by-product hydrogen chloride).
4. The energy utilization rate is enhanced and the equipment size is reduced. The present application integrates the high-gravity reactor, the high-pressure kettle and the rectifying tower as one equipment, thus reducing the heat and momentum loss during the transfer of materials between equipment, improving the energy utilization rate, and reducing the total foot print of the apparatus by more than half.

In addition, in a further preferred embodiment, the system further comprises a condensing component in communication with the gas exit passageway of the reaction apparatus, thus cooperating with the flow-deflecting plates to form a plurality of condensation defense lines.

In addition, the present application further provides a method for preparing trifluoroethane through continuous reaction, comprising:
S1: pumping vinylidene chloride and hydrogen fluoride into the submersible pump and the rotary cutting component of the reaction apparatus according to any one of claims 1-7 according to a set ratio through a first liquid feed pipeline;
S2: pumping a fluid entraining catalyst particles into the rotary cutting component through a circulating pipeline, so that the rotary cutting component cuts the fluid entraining the catalyst particles into micro/nanoscale fluid micro elements and thereby the catalyst particles catalyze the vinylidene chloride and hydrogen fluoride to generate trifluoroethane; and
S3: heating the reaction apparatus to a set temperature through a jacket arranged on an outer sidewall of the reaction apparatus such that trifluoroethane is discharged through the gas exit passageway.

Specifically, in the present application, the raw materials vinylidene chloride 1 and hydrogen fluoride 2 are firstly continuously fed into a feed port of the built-in high-gravity reactor according to a certain ratio, which, together with the catalyst liquid entrained in the circulating feed liquid, are sheared and crushed into liquid drops, liquid filaments and liquid films in the rotary filler, fully mixed and quickly reacted. After passing through the high-gravity reactor, the reaction liquid and the catalyst enter the lower space of the inner chamber of the jacket reaction kettle with flow-deflecting plates at the top of the reaction kettle. The reaction kettle is heated by jacket steam to maintain a certain temperature. The product 1,1,1-trifluoroethane (HFC-143a), the intermediate product 1,1-difluoroethane (HCFC-142b), and mixed gas obtained through gasification of the by-product hydrogen chloride are evaporated from the top of the reaction kettle through the flow-deflecting plates. The liquid at the bottom of the reaction kettle is circulated back to the high-gravity reactor through the submersible pump 5 for continuous reaction. In the flow-deflecting plates at the top of the reaction kettle, the mixed gas and the reflux condensate are in countercurrent contact. The heavy component 1,1-difluoroethane (HCFC-142b) in the gas is mostly condensed and washed into the liquid phase, and the mixed gas is further refined. The refined mixed gas flows out of the flow-deflecting plates at the top of the reaction kettle and is fed into the condenser 6. In the condenser, impurities such as intermediate product 1,1-difluoroethane (HCFC-142b) with high boiling points are condensed, which, as the aforementioned reflux liquid, are returned to the reaction kettle through the flow-deflecting plates at the top of the reaction kettle. The product 1,1,1-trifluoroethane (HFC-143a) and by-product hydrogen chloride gas are discharged from a gas phase outlet of the condenser and directed to a subsequent refining separation unit, thus obtaining high-purity product 1,1,1-trifluoroethane (HFC-143a) and by-product hydrogen chloride.

Specifically, the present application further optimizes the entire process parameters. The level of the high gravity field in the high-gravity reactor is 30-1500 g, more preferably 100-600 g. The temperature of the reaction kettle is maintained at 60-110° C., preferably 80-90° C. The pressure of the reaction kettle is maintained at 1.2 MPa. The molar ratio of raw materials hydrogen fluoride to vinylidene chloride fed into the high-gravity reactor is 2-5:1, more preferably 3-4:1. The ratio of the mass flow of the circulating liquid passing through the submersible pump to the sum of the mass flow of the newly fed raw materials vinylidene chloride and hydrogen fluoride is 5-15:1, more preferably 8-10:1. The liquid-phase catalyst comprises but is not limited to SnCl4, halosulfonic acid, and a mixture thereof. The mass ratio of the catalyst molecules in the liquid-phase catalyst in the circulating liquid to the newly fed vinylidene chloride is 0.1-0.3:1.

It can be seen that the method arranged by the present application has the following advantages:
1. The reaction efficiency is improved and the utilization rate of raw materials is enhanced. Since the reaction feed liquid is quickly mixed after entering the high-gravity reactor, part of the coagulated and coated catalyst micelles are crushed, the active site of the catalyst is fully exposed, and the reaction is fast. Moreover, since there is a large amount of unreacted hydrogen fluoride contained in the circulating liquid, the hydrogen fluoride is therefore too excessive in the reaction process. The above two reasons result in vinylidene chloride being rapidly reacted, thus inhibiting the self-polymerization and significantly improving the utilization rate of raw materials. After adopting the present application, the utilization rate of raw materials vinylidene chloride can reach more than 98%.
2. The production efficiency and safety are improved. As described above, the present application can effectively inhibit the occurrence of the self-polymerization side reaction of vinylidene chloride, prevent the polymers and tar-like substances generated by self-polymerization from coating the equipment and catalyst, and ensure long-term continuous production without frequent shut-down for maintenance. Hydrogen fluoride leakage is a very serious safety accident. The present application uses the built-in submersible pump to reduce the risk of leakage of a large amount of hydrogen fluoride in the circulating liquid. In addition, the present application couples the separation apparatus (flow-deflecting plates at the top of the reaction kettle) with the reaction kettle to reduce the risk of leakage during pipeline transportation. Therefore, the safety of the present application is relatively high.
3. The separation effect is good and the product purity is high. The unique design of the flow-deflecting plates at the top of the reaction kettle in the present application allows for full contact and heat exchange between the reflux condensate and the rising gas. The heavy component impurities entrained in the steam are washed into the reflux liquid, and a small amount of condensed products in the reflux liquid are evaporated into the gas, thus improving the purity of the product. After adopting the present application, the mass fraction of HFC-143a in the product can reach 98% (containing no by-product hydrogen chloride).
4. The energy utilization rate is enhanced and the equipment size is reduced. The present application integrates the high-gravity reactor, the high-pressure kettle and the rectifying tower as one equipment, thus reducing the heat and momentum loss during the transfer of materials between equipment, improving the energy utilization rate, and reducing the total foot print of the apparatus by more than half.

Some specific examples are arranged hereinbelow to deepen understanding of the inventive concept of the present application.

Example 1

The apparatus and method arranged by the present application are used for preparing 1,1,1-trifluoroethane (HFC-143a) through continuous reaction, using catalyst SnCl4. The mass ratio of catalyst molecules to newly fed vinylidene chloride is 0.2:1, wherein the molar flow ratio of the feed of hydrogen fluoride to the feed of 1,1,1-trifluoroethane (HFC-143a) is 3:1, the reaction temperature is 85° C., the system pressure is maintained at 1.2 MPa, the high gravity level of the built-in high-gravity reactor is 500 g, the recycle ratio is 8:1. The measured conversion rate of vinylidene chloride is 99.3% and the mass fraction of HFC-143a in the outlet gas (containing no hydrogen chloride) is 99.8%.

Example 2

The apparatus and method arranged by the present application are used for preparing 1,1,1-trifluoroethane (HFC-143a) through continuous reaction, using catalyst SnCl4. The mass ratio of catalyst molecules to newly fed vinylidene chloride is 0.2:1, wherein the molar flow ratio of the feed of hydrogen fluoride to the feed of 1,1,1-trifluoroethane (HFC-143a) is 4:1, the reaction temperature is 85° C., the system pressure is maintained at 1.2 MPa, the high gravity level of the built-in high-gravity reactor is 600 g, the recycle ratio is 10:1. The measured conversion rate of vinylidene chloride is 99.8% and the mass fraction of HFC-143a in the outlet gas (containing no hydrogen chloride) is 99.9%.

Example 3

The apparatus and method arranged by the present application are used for preparing 1,1,1-trifluoroethane (HFC-143a) through continuous reaction, using catalyst SnCl4. The mass ratio of catalyst molecules to newly fed vinylidene chloride is 0.2:1, wherein the molar flow ratio of the feed of hydrogen fluoride to the feed of 1,1,1-trifluoroethane (HFC-143a) is 3:1, the reaction temperature is 80° C., the system pressure is maintained at 1.2 MPa. the high gravity level of the built-in high-gravity reactor is 300 g, the recycle ratio is 8:1. The measured conversion rate of vinylidene chloride is 98.9% and the mass fraction of HFC-143a in the outlet gas (containing no hydrogen chloride) is 99.4%.

Example 4

The apparatus and method arranged by the present application are used for preparing 1,1,1-trifluoroethane (HFC-143a) through continuous reaction, using catalyst SnCl4. The mass ratio of catalyst molecules to newly fed vinylidene chloride is 0.3:1, wherein the molar flow ratio of the feed of hydrogen fluoride to the feed of 1,1,1-trifluoroethane (HFC-143a) is 4:1, the reaction temperature is 90° C., the system pressure is maintained at 1.2 MPa, the high gravity level of the built-in high-gravity reactor is 500 g, the recycle ratio is 10:1. The measured conversion rate of vinylidene chloride is 99.9% and the mass fraction of HFC-143a in the outlet gas (containing no hydrogen chloride) is 99.7%.

Comparative Example 1

The apparatus and method arranged by the present application are used for preparing 1,1,1-trifluoroethane (HFC-143a) through continuous reaction, using catalyst SnCl4. The mass ratio of catalyst molecules to newly fed vinylidene chloride is 0.2:1, wherein the molar flow ratio of the feed of hydrogen fluoride to the feed of 1,1,1-trifluoroethane (HFC-143a) is 1:1, the reaction temperature is 85° C. the system pressure is maintained at 1.2 MPa, the high gravity level of the built-in high-gravity reactor is 600 g, the recycle ratio is 9:1. The measured conversion rate of vinylidene chloride is 96.8% and the mass fraction of HFC-143a in the outlet gas (containing no hydrogen chloride) is 98.2%.

Comparative Example 2

The apparatus and method arranged by the present application are used for preparing 1,1,1-trifluoroethane (HFC-143a) through continuous reaction, using catalyst SnCl4. The mass ratio of catalyst molecules to newly fed vinylidene chloride is 0.2:1, wherein the molar flow ratio of the feed of hydrogen fluoride to the feed of 1,1,1-trifluoroethane (HFC-143a) is 3:1, the reaction temperature is 85° C., the system pressure is maintained at 1.2 MPa, the high gravity level of the built-in high-gravity reactor is 10 g, the recycle ratio is 8:1. The measured conversion rate of vinylidene chloride is 82.7% and the mass fraction of HFC-143a in the outlet gas (containing no hydrogen chloride) is 92.1%.

Comparative Example 3

The apparatus and method arranged by the present application are used for preparing 1,1,1-trifluoroethane (HFC-143a) through continuous reaction using catalyst SnCl4. The mass ratio of catalyst molecules to newly fed vinylidene chloride is 0.2:1, wherein the molar flow ratio of the feed of hydrogen fluoride to the feed of 1,1,1-trifluoroethane (HFC-143a) is 3:1, the reaction temperature is 85° C., the system pressure is maintained at 1.2 MPa, the high gravity level of the built-in high-gravity reactor is 500 g, the recycle ratio is 2:1. The measured conversion rate of vinylidene chloride is 83.3% and the mass fraction of HFC-143a in the outlet gas (containing no hydrogen chloride) is 87.8%.

Comparative Example 4

The apparatus and method arranged by the present application are used for preparing 1,1,1-trifluoroethane (HFC-143a) through continuous reaction, using catalyst SnCl4. The mass ratio of catalyst molecules to newly fed vinylidene chloride is 0.2:1, wherein the molar flow ratio of the feed of hydrogen fluoride to the feed of 1,1,1-trifluoroethane (HFC-143a) is 3:1, the reaction temperature was 50° C., the system pressure is maintained at 1.2 MPa, the high gravity level of the built-in high-gravity reactor is 500 g, the recycle ratio is 8:1. The measured conversion rate of vinylidene chloride is 91.6% and the mass fraction of HFC-143a in the outlet gas (containing no hydrogen chloride) is 92.8%.

Comparative Example 5

The apparatus and method arranged by the present application are used for preparing 1,1,1-trifluoroethane (HFC-143a) through continuous reaction, using catalyst SnCl4.

The mass ratio of catalyst molecules to newly fed vinylidene chloride is 0.2:1, wherein the molar flow ratio of the feed of hydrogen fluoride to the feed of 1,1,1-trifluoroethane (HFC-143a) is 3:1, the reaction temperature was 120° C., the system pressure is maintained at 1.2 MPa, the high gravity level of the built-in high-gravity reactor is 500 g, the recycle ratio is 8:1. The measured conversion rate of vinylidene chloride is 98.6% and the mass fraction of HFC-143a in the outlet gas (containing no hydrogen chloride) is 85.9%.

By comprehensive analysis of the results of the examples and comparative examples, it can be concluded that the apparatus and method arranged by the present application can effectively improve the efficiency of reaction and separation within the claimed process operating parameters, and the conversion rate of vinylidene chloride and the purity of HFC-143a are significantly improved.

From the above, it can be seen that the present application discloses an apparatus and method for preparing 1,1,1-trifluoroethane (HFC-143a) through continuous reaction, which use vinylidene chloride (VDC) as raw material to obtain high-purity 1,1,1-trifluoroethane, the reaction time is reduced by half compared with the existing process, and the utilization rate of raw material is more than 97%. The core technology of the present application is the high-gravity enhanced reaction technology, which utilizes the shearing, crushing, and rapid mixing effects of the high-gravity reactor on the fluid to fully carry out the main reaction and inhibit the side reaction. The core equipment of the present application is a self-designed reaction, separation and circulation integrated apparatus of the built-in high-gravity reactor. Through equipment integration and reaction and separation coupling, the production efficiency is effectively improved. In addition, the built-in circulation system reduces the risk of leakage of hydrogen fluoride. The apparatus and method proposed by the present application are safe and efficient, and have important reference significance for improving the existing production process.

Apparently, the above embodiments of the present application are only exemplary for the purpose of clearly describing the present application rather than limiting the implementation of the present application. For those skilled in the art, on the basis of the above description, other different forms of modifications or changes may be made. It is not possible to exhaust all the implementations herein. Any apparent changes or variations arising from the technical solutions of the present application are still within the scope of protection of the present application.

The invention claimed is:

1. A system for preparing trifluoroethane through continuous reaction, comprising:
   a vinylidene chloride liquid feed pipeline and a hydrogen fluoride feed pipeline, the vinylidene chloride liquid feed pipeline and the hydrogen fluoride feed pipeline are in communication with a rotary cutting component and a submersible pump;
   a housing comprising a reaction chamber body and a gas exit passageway in communication with the reaction chamber body;
   the rotary cutting component arranged inside the reaction chamber body, wherein the rotary cutting component comprises an annular filler and a liquid distributor located in a center of the annular filler, and threads are formed on a surface of the annular filler used for cutting a fluid into micro/nanoscale fluid micro elements;
   the submersible pump arranged at a bottom of the reaction chamber body; and
   a flow deflector comprising two sets of flow-deflecting plates, each set of said flow-deflecting plates comprising a plurality of flow-deflecting plates, the two sets of flow-deflecting plates being respectively fixed on two opposing sidewalls, and adjacent two flow-deflecting plates being in offset alignment, wherein each flow-deflecting plate is tilted upwards along a direction towards the sidewall on which the flow-deflecting plate is fixed, wherein a plurality of protrusions are formed on a lower surface of each flow-deflecting plate,
   wherein the submersible pump is coupled with a discharge pipeline, and the rotary cutting component is coupled with a feed pipeline.

2. The system according to claim 1, wherein the diameter of the protrusion gradually increases along a direction towards corresponding sidewall.

3. The system according to claim 2, wherein the reaction apparatus further comprises:
 a condensation disturbance component comprising a rotating shaft and a condenser surrounding the rotating shaft, the rotating shaft being used for throwing condensed liquid drops on the condenser into the rotary cutting component.

4. The system according to claim 1, wherein each set of said flow-deflecting plates comprises 3-25 flow-deflecting plates.

5. The system according to claim 1, wherein the system further comprises:
 a condensing component in communication with the gas exit passageway of the reaction apparatus.

6. A method for preparing trifluoroethane through continuous reaction, comprising:
 pumping vinylidene chloride and hydrogen fluoride into the submersible pump and the rotary cutting component of the system according to claim 1 according to a set ratio through a first liquid feed pipeline;
 pumping a fluid entraining catalyst particles into the rotary cutting component through a circulating pipeline, so that the rotary cutting component cuts the fluid entraining the catalyst particles into micro/nanoscale fluid micro elements and thereby the catalyst particles catalyze the vinylidene chloride and hydrogen fluoride to generate trifluoroethane; and
 heating the reaction apparatus to a set temperature through a jacket arranged on an outer sidewall such that the trifluoroethane is discharged through the gas exit passageway.

* * * * *